(12) United States Patent
Sarid et al.

(10) Patent No.: US 8,758,777 B2
(45) Date of Patent: Jun. 24, 2014

(54) PHARMACEUTICAL COMPOSITIONS COMPRISING WATER-SOLUBLE SULFONATE-PROTECTED NANOPARTICLES AND USES THEREOF

(75) Inventors: Ronit Sarid, Or-Yehuda (IL); Aharon Gedanken, Givataim (IL); Dana Baram-Pinto, Yokneam Moshava (IL)

(73) Assignee: Bar-Ilan University, Tel-Aviv (IL)

(*) Notice: Subject to any disclaimer, the term of this patent is extended or adjusted under 35 U.S.C. 154(b) by 54 days.

(21) Appl. No.: 13/134,926

(22) Filed: Jun. 21, 2011

(65) Prior Publication Data

US 2012/0027809 A1 Feb. 2, 2012

Related U.S. Application Data

(60) Provisional application No. 61/344,266, filed on Jun. 21, 2010.

(51) Int. Cl.
*A61K 9/14* (2006.01)
*A61K 31/28* (2006.01)
*A61P 31/00* (2006.01)
*A61P 31/04* (2006.01)
*A61P 31/18* (2006.01)
*A61P 31/22* (2006.01)
*A61P 31/14* (2006.01)
*A61P 31/12* (2006.01)

(52) U.S. Cl.
USPC ............ 424/400; 514/495; 977/773; 977/915

(58) Field of Classification Search
None
See application file for complete search history.

(56) References Cited

U.S. PATENT DOCUMENTS

2006/0269485 A1* 11/2006 Friedman et al. ............... 424/45
2010/0056485 A1 3/2010 Park

FOREIGN PATENT DOCUMENTS

DE 10342258 A1 * 4/2005 ............ A61K 33/38
WO 20100040111 A1 4/2010

OTHER PUBLICATIONS

Zou, X. et al. "Mercaptoethane sulfonate protected, water-soluble god and silver nanoparticles: Synthesis, characterization and their building multilayer films with polyaniline via ion-dipole interactions" J. of Colloid and Interface Science, 2006, v. 295, 401-408.*
Cho, K.-H. et al. "The study of antimicrobial activity and preservative effects of nanosilver ingredient" Electrochimica Acta, 2005, v. 51, 956-960.*
Baram-Pinto, D. et al. "Inhibition of Herpes Simplex Virus Type 1 Infection by Silver nanoparticles capped with mercaptoethane sulfonate" Bioconjugate Chem, 2009, v. 20, 1497-1502.*

(Continued)

*Primary Examiner* — Mina Haghighatian
*Assistant Examiner* — Erin Hirt
(74) *Attorney, Agent, or Firm* — Browdy and Neimark, PLLC

(57) ABSTRACT

The present invention provides pharmaceutical compositions comprising water-soluble sulfonate-protected nanoparticles, more particularly, pharmaceutical compositions comprising water-soluble sulfonate-protected silver or gold nanoparticles. The pharmaceutical compositions of the invention are useful in prevention or treatment of infections or conditions or disorders caused by microorganisms capable of binding to heparan sulfate, e.g., herpes simplex viruses.

19 Claims, 8 Drawing Sheets
(1 of 8 Drawing Sheet(s) Filed in Color)

(56) References Cited

OTHER PUBLICATIONS

Manorama, S. V. et al. "Photostabilization of dye on anatase titania nanoparticles by polymer capping" Journal of Physics and Chemistry of Solids, 2002, v. 63, 135-143.*

Baram-Pinto et al; "Inhibition of Herpes Simplex Virus Type 1 Infection by Silver Nanoparticles Capped with Mercaptoethane Sulfonate" Bioconjugate Chemistry 20, pp. 1497-1502. (2009).

Bastus N.G et al; "Homogeneous Conjugation of Peptides onto Gold Nanoparticles Enhances Macrophage Response" American Chemical Society 3, 6, pp. 1335-1344. (2009).

Bowman M.C et al; "Inhibition of HIV Fusion with Multivalent Gold Nanoparticles".Journal of the American Chemical Society 130, pp. 6896-6897. (2008).

Flavio Manea et al; "Multivalent, Saccharide-Functionalized Gold Nanoparticlesas Fully Synthetic Analogs of Type a *Neisseria meningitidis* Antigens" Advanced Materials 20, pp. 4348-4352. (2008).

Gong Y et al; "Evidence of dual sites of action of dendrimers: SPL-2999 inhibits both virus entry and late stages of herpes simplex virus replication" Antiviral Research 55, pp. 319-329. (2002).

Gong E et al; "Evaluation of dendrimer SPL7013, a lead microbicide candidate against herpes simplex viruses"., Antiviral Research 68, pp. 139-14. (2005).

Hall P.R.et al; "Multivalent Presentation of Antihantavirus Peptides on Nanoparticles Enhances Infection Blockade" Antimicrobial Agents and Chemotherapy vol. 52, No. 6, pp. 2079-2088. (2008).

Herold B.C et al; "Mandelic Acid Condensation Polymer: Novel Candidate Microbicide for Prevention of Human Immunodeficiency Virus andHerpes Simplex Virus Entry" Journal of Virology vol. 76, No. 22, pp. 11236-11244. (2002).

Lytton-Jean a.K et al; ".A Thermodynamic Investigation into the Binding Properties of DNA Functionalized Gold Nanoparticle Probes and Molecular Fluorophore Probes." Journal of the American Chemical Society 127 pp. 12754-12755. (2005).

Ma L.L. et al; "Small Multifunctional Nanoclusters (Nanoroses) for Targeted Cellular Imaging and Therapy" American Chemical Society 3, pp. 2686-2696. (2009).

Montet X. et al; "Multivalent Effects of RGD Peptides Obtained by Nanoparticle Display" Journal of Medinical. Chemistry 49, pp. 6087-6093. (2006).

Mrinmoy De et al"Applications of Nanoparticles in Biology" Advanced Materials 20, pp. 4225-4241. (2008).

Nam J.M et al; "Bio-Bar-Code-Based DNA Detection with PCR-like Sensitivity", Journal of the American Chemical Society 126, pp. 5932-5933. (2004).

Niemeyer C. M., "Nanoparticles, Proteins, and Nucleic Acids: Biotechnology Meets Materials Science", Angewandte Chemie Internationl Edition 40, pp. 4128-4158. (2001).

Phillips R.L.et al; "Rapid and Efficient Identification of Bacteria Using Gold-Nanoparticle—Poly(paraphenyleneethynylene) Constructs" Angewandte Chemie Internationl Edition. 47, pp. 2590-2594. (2008).

Rozhkova E.A. et al; "High-Performance Nanobio Photocatalyst for Targeted Brain Cancer Therapy" American Chemical Society 9, pp. 3337-3342. (2009).

Rusnati M et al; "Sulfated K5 *Escherichia coli* polysaccharide derivatives: a novel class of candidate antiviral microbicides" Pharmacology & Therapeutics 123 pp. 310-322. (2009).

Stoeva S.I.et al; "Multiplexed Detection of Protein Cancer Markers with Biobarcoded Nanoparticle Probes" Journal of the American Chemical Society 128, pp. 8378-8379. (2006).

Wang X et al; "HFT-T, a Targeting Nanoparticle, Enhances Specific Delivery of Paclitaxel to Folate Receptor-Positive Tumors" .American Chemical Society Nano 3, pp. 3165-3174. (2009).

Willner I et al; "Nanoparticle—enzyme hybrid systems for nanobiotechnology", Federation of European Biochemical Societies Journal 274, pp. 302-309. (2007).

Zou X et al; "Mercaptoethane sulfonate protected, water-soluble gold and silver nanoparticles: Syntheses, characterization and their building multilayer films with polyaniline via ion—dipole interactionsColloid Interface" Journal of Colloid and Interface Science 295, pp. 401-408. (2006).

Baram-Pinto et al; "Inhibition of HSV-1 Attachment, Entry, and Cell-to-Cell Spread by Functionalized Multivalent Gold Nanoparticles" Small 6, No. 9, pp. 1044-1050. (2010).

* cited by examiner

PHARMACEUTICAL COMPOSITIONS COMPRISING WATER-SOLUBLE SULFONATE-PROTECTED NANOPARTICLES AND USES THEREOF

CROSS-REFERENCE TO RELATED APPLICATIONS

The present application claims the benefit of U.S. Provisional Patent Application No. 61/344,266, filed Jun. 21, 2010, the entire content of which is herewith incorporated by reference in its entirety as if fully disclosed herein.

BACKGROUND

The present invention relates to pharmaceutical compositions comprising water-soluble sulfonate-protected nanoparticles, more particularly, silver or gold nanoparticles. These compositions are useful in prevention or treatment of infections, conditions or disorders caused by microorganisms capable of binding to heparin sulfate, such as herpes simplex viruses.

Viruses pose significant global health challenges, while effective antiviral therapies continue to be hampered by the emergence of resistant viral strains and adverse side effects associated with prolonged use (Abdel-Haq N. et al., *Indian. J. Pediatr.*, 2006, 73, 313-321; Baleux et al., *Bioconjugate Chem.*, 2009, 20, 1497-1502; Enquist et al., *J. Virol.*, 2009, 83, 5296-5308; Flexner et al., *Nature Reviews Drug Discovery*, 2007, 6, 959-966; each incorporated by reference herein in its entirety). Such obstacles have limited the extent of antiviral drugs in clinical use as compared with anti-bacterial drugs, and the development of safe and potent alternatives is needed. Multidisciplinary research efforts, integrated with classical epidemiology and clinical approaches, are therefore crucial for the development of alternative strategies towards improved antiviral drugs (Enquist et al., 2009)

Biological interactions are often multivalent in nature. Thus, recognition and cell signal transduction events often involve multiple copies of receptors and ligands that bind in a coordinated manner, resulting in drastically enhanced specificity, efficiency and strength of such interactions relative to their monovalent counterparts (Mammen et al., *Angew. Chem. Int. Ed.*, 1998, 37, 2755-2794, incorporated by reference herein in its entirety). The attachment and entry of viruses into the host cells is an outcome of such multivalent interactions between viral surface components and cell membrane receptors (Mammen et al., 1998; Fields et al., in *Fields' Virology*, 5th Ed.; Wolters Kluwer Health/Lippincott Williams & Wilkins: Philadelphia, 2007; Flint et al., in *Principles of Virology: Molecular Biology, Pathogenesis, and Control of Animal Viruses*, 2nd Ed.; ASM Press: Washington, D.C., 2004; each incorporated by reference herein in its entirety). Interfering with these recognition events, and thereby blocking viral entry into the cells, is one of the most promising strategies being pursued to develop new antiviral drugs and preventive topical microbicides (Bowman et al., *J. Am. Chem. Soc.*, 2008, 130, 6896-6897; Rusnati et al., *Pharmacol. Ther.*, 2009, 123, 310-322; each incorporated by reference herein in its entirety).

The successful incorporation of functionalized nanomaterials in biomedical applications in recent years is derived from the combination of the inherent physical and chemical properties of nanomaterials with those of the surface bound ligands (Mrinmoy et al., *Adv. Mater.*, 2008, 20, 4225-4241; Niemeyer, *Angew. Chem. Int. Ed*, 2001, 40, 4128-4158; Willner et al., *FEBS Journal*, 2007, 274, 302-309; each incorporated by reference herein in its entirety). As surface bound ligands, these biomolecules or their synthetic analogues are spatially directed, and render their carrier nanomaterials into multivalent biological effecter compounds (Hall et al., *Antimicrob. Agents Chemother.*, 2008, 52, 2079-2088; Flavio Manea et al., *Adv. Mater.*, 2008, 20, 4348-4352; Montet et al., *J. Med. Chem.*, 2006, 49, 6087-6093; each incorporated by reference herein in its entirety). Such nano-biological constructs also generate an increased local concentration of the surface ligands over free unbound molecules and enhance ligand binding affinity to specific targets (Bowman et al., 2008; Bastus et al., *ACS Nano*, 2009, 3, 1335-1344; Lytton-Jean et al., *J. Am. Chem. Soc.*, 2005, 127, 12754-12755; Ma et al., *ACS Nano*, 2009, 3, 2686-2696; each incorporated by reference herein in its entirety). Indeed, this approach has previously been used to develop nanoparticle-based targeted drug carriers (Wang et al., *ACS Nano*, 2009, 3, 3165-3174; incorporated by reference herein in its entirety), rapid pathogen detection (Phillips et al., *Angew. Chem. Int. Ed*, 2008, 47, 2590-2594; incorporated by reference herein in its entirety), biomolecular sensing (Nam et al., *J. Am. Chem. Soc.*, 2004, 126, 5932-5933; Stoeva et al., *J. Am. Chem. Soc.*, 2006, 128, 8378-8379; each incorporated by reference herein in its entirety), as well as nanoparticle-based cancer therapies (Rozhkova et al., *Nano Lett.*, 2009, 9, 3337-3342; incorporated by reference herein in its entirety). The use of functionalized nanoparticles can be extended to the development of antiviral drugs that act by interfering with viral infection, in particular during attachment and entry. The efficacy of the antiviral multivalent nanoparticles approach has been recently illustrated with the demonstration that mercaptobenzoic acid modified gold nanoparticles convert a weakly binding small molecule into a multivalent conjugate that efficiently inhibits HIV-1 infection (Bowman et al., 2008). Based on similar principles, glycol-functionalized nanoparticles have recently been used for optical detection of viruses (Nikura et al., *Bioconjugate Chem.*, 2009, 20, 1848-1852; incorporated by reference herein in its entirety).

Herpes simplex virus (HSV)-associated diseases are among the most widespread infections, affecting about 60-95% of human adults. These diseases are incurable and persist during the lifetime of the host, often in latent form. The clinical manifestations of such infections are variable and influenced by the portal of viral entry, age of the host, degree of host immunocompetence, primary or secondary nature of the disease and other unknown factors. Clinical presentations of HSV infection range from asymptomatic infection to mucocutaneous conditions such as labial herpes, also known as fever blisters or cold sores, keratitis and genital herpes, as well as central nervous system complications such as neonatal herpes and herpetic encephalitis that could have fatal outcome. Recurrent mucocutaneous disease episodes appear in 15-40% of HSV-infected individuals. Of note, genital herpes is currently considered one of the most prevalent sexually transmitted infections worldwide.

Current management approach to HSV infection does not target viral eradication, but rather the prevention of transmission, suppression of recurrence, attenuation of clinical course and complications, as well as promotion of healing. Topical, oral, or intravenous Acyclovir and other nucleoside derivatives have been approved for treatment of HSV infections and are widely used. However, the emergence of resistant viral strains, mainly after prolonged treatment in immunocompromised patients, is one of the main reasons for continuous search of new anti-herpes drugs that can inhibit infection by both wild-type viruses and drug-resistant strains.

Glycoprotein C (gC) mediates high affinity attachment of the HSV-1 to cells by binding to glycosaminoglycans (GAGs) of heparan sulfate (HS) or to chondroitin sulfate on the cell surface. The significance of this interaction is highlighted by the reduced HSV-1 infection in the absence of either viral gC or cell surface heparan sulfate (Arvin et al., in *Human Herpesviruses: Biology, Therapy, and Immunoprophylaxis*, Cambridge: New York, 2007; Mardberg et al., *J. Gen. Virol.*, 2001, 82, 1941-1950; Reske et al., *Rev. Med. Virol.*, 2007, 17, 205-215; each incorporated by reference herein in its entirety).

Many pathogenic microorganisms, like HSV, express on their surface proteins that are capable of binding to heparan sulfate, and these interactions appear important for their infectivity. Compounds that mimic heparan sulfate chains, such as the sulfated polysaccharide heparin, were shown to inhibit HSV attachment to cells, suggesting that these compounds act via competition with heparan sulfate chains for binding to the virus attachment proteins. Interference with some post-attachment steps in HSV infection by these compounds has also been suggested.

Previously, sulfated and sulfonated polysaccharides, as well as several other polyanionic compounds including dendrimers, have been investigated as potential anti-HSV-1 agents based on the principle that they mimic heparan sulfate and compete for the binding of the virus to the cell. These candidate microbicides act by blocking cell surface receptors-virus interactions, thereby inhibiting virus attachment/entry, and possibly blocking cell-to-cell spread as well (Rusnati et al., 2009; Gong et al., *Antiviral Res.*, 2002, 55, 319-329; Gong et al., *Antiviral Res.*, 2005, 68, 139-146; Herold et al., *J. Virology*, 2002, 11236-11244; each incorporated by reference herein in its entirety). Nanoparticle-bound ligands have potentially enhanced affinity to interact with target molecules, due to their spatial orientation and large surface area.

Zou et al. (*J. Colloid Interface Sci.*, 2006, 295, 401-408; incorporated by reference herein in its entirety) discloses a one-phase method for the synthesis of mercaptoethane sulfonate-protected, water-soluble gold and silver nanoparticles (Au-MES NPs and Ag-MES NPs). As described, both Au-MES NPs and Ag-MES NPs are soluble in water up to 2.0 mg/ml and the stability of Au-MES NPs is much better than that of Ag-MES NPs. When dissolved in water, they behave like a polyanion and can be used to build multilayer films with polyaniline (PANI) by way of layer-by-layer.

US 2010/056485 (incorporated by reference herein in its entirety) discloses a silver nanoparticles-based antimicrobial composition, comprising an amphiphilic molecule having at least one hydrophilic group, e.g., carboxylate, sulfonate, sulfate, sulfinate, phosphate, phosphinate, phosphonate, and quaternary amine, and at least one hydrophobic group attached thereto, wherein at least one silver nanoparticle is in contact with the amphiphilic molecule. As stated in this publication, the antimicrobial properties of this composition derive from the silver nanoparticles.

SUMMARY OF THE INVENTION

It has been found, in accordance with the present invention, that water-soluble sulfonate-protected nanoparticles mimicking the polysulfonated heparan sulfate, more particularly mercaptoethane sulfonate-protected silver or gold nanoparticles, effectively inhibit herpes simplex virus-1 (HSV-1) infection of Vero cells without affecting cell viability, suggesting that such nanoparticles can efficiently be used for prevention or treatment of infections, conditions or disorders caused by microorganisms capable of binding to heparan sulfate, e.g., particular viruses of the herpesviridae family such as herpes simplex viruses (see also Baram-Pinto et al., *Bioconjug Chem.*, 2009, 20(8), 1497-1502; incorporated by reference herein in its entirety).

In one aspect, the present invention thus provides a pharmaceutical composition, comprising water-soluble sulfonate-protected nanoparticles, or a pharmaceutically acceptable salt thereof, and a pharmaceutically acceptable carrier.

In another aspect, the present invention relates to a method for prevention or treatment of an infection, condition or disorder caused by a microorganism capable of binding to heparan sulfate in an individual in need, said method comprising administering to said individual a prophylactically or therapeutically effective amount of a pharmaceutical composition comprising water-soluble sulfonate-protected nanoparticles or a pharmaceutically acceptable salt thereof.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
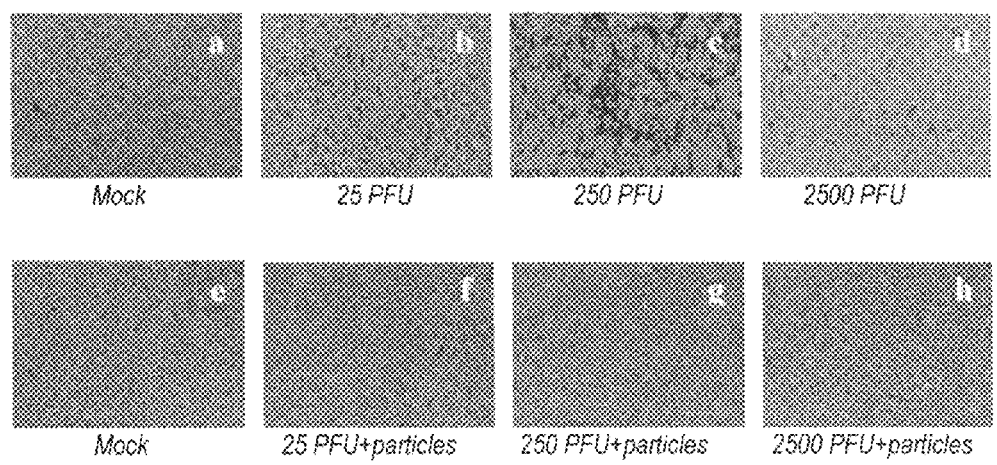
FIG. 1 shows light microscope images of HSV-1-infected Vero cells. Cells were infected with various virus dilutions in the presence or absence of 400 μg/ml of mercaptoethane sulfonate-protected silver nanoparticles (Ag-MES NPs), and pictures were taken at 48 hours post infection. Panels A and E are without virus (Mock); panels A-D are without Ag-MES NPs; panels E-H are with Ag-MES NPs; and panels B and F, C and G, and D and H show cells infected with 25, 250 and 2500 virus plaque forming units (PFU), respectively.

In one aspect, the present invention provides a pharmaceutical composition comprising water-soluble sulfonate-protected nanoparticles, or a pharmaceutically acceptable salt thereof, and a pharmaceutically acceptable carrier.

The term "water-soluble sulfonate-protected nanoparticles", as used herein, refers to any sulfonate-protected nanoparticles, i.e., nanoparticles covered with sulfonate-containing groups, which are water-soluble, i.e., capable of dissolving in water or aqueous solutions to form a homogeneous solution.

In certain embodiments, the pharmaceutical composition of the present invention comprises nanoparticles made of a metal or metal oxide, capable of binding to sulfides, carboxylic acids or amines.

In certain particular embodiments, the nanoparticles are made of a metal capable of binding to sulfides, carboxylic acids or amines, more particularly, a non-active metal, i.e., a metal that is not spontaneously oxidized in air, such as a noble metal. Examples of such metals include, without being limited to, silver (Ag), gold (Au), platinum (Pt), palladium (Pd), ruthenium (Ru), rhodium (Rh), osmium (Os) and iridium (Ir). In more particular embodiments, the nanoparticles are made of Ag or Au.

In other particular embodiments, the nanoparticles are made of a metal oxide capable of binding to sulfides, carboxylic acids or amines. Non-limiting examples of metal oxide that may be used for the preparation of the nanoparticles include ZnO, MgO, CuO, $Fe_3O_4$, $TiO_2$, $Al_2O_3$, and $SiO_2$.

The pharmaceutical composition of the present invention may comprise water-soluble sulfonate-protected nanoparticles having a size in the range of 3-30 nm, preferably 3-20 nm, more preferably 3-10 nm. In particular embodiments, the nanoparticles comprised within the pharmaceutical composition of the invention are in size of 3-4 nm.

In certain embodiments, the water-soluble sulfonate-protected nanoparticles comprised within the pharmaceutical composition of the present invention are nanoparticles covered with a sulfonate of the general formula -A-R—SO3H, wherein R is a divalent hydrocarbyl; and A is —S—, —NH— or —O—CO—, preferably —S—, linked to said divalent hydrocarbyl at position omega ($\omega$) that is most remote from the SO3H group.

The term "divalent hydrocarbyl" refers to a divalent radical containing only carbon and hydrogen atoms that may be saturated or unsaturated, linear or branched, cyclic or acyclic, or aromatic, which may be derived from a C1-C20 alkane, C2-C20 alkene, C2-C20 alkyne, C3-C20 cycloalkane, C3-C20 cycloalkene, C6-C14 monocyclic or polycyclic aromatic ring, or C6-C14 monocyclic or polycyclic aromatic ring linked to a C1-C20 alkyl, C2-C20 alkenyl or C2-C20 alkynyl.

The term "C1-C20 alkane" typically means a straight or branched hydrocarbon having 1-20 carbon atoms and includes, e.g., methane, ethane, n-propane, isopropane, n-butane, sec-butane, isobutane, tert-butane, n-pentane, 2,2-dimethylpropane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, icosane and the like. Preferred are C2-C6 alkanes, more preferably C2-C4, most preferably ethane or propane. The terms "C2-C20 alkene" and "C2-C20 alkyne" typically mean straight and branched hydrocarbon having 2-20 carbon atoms and 1 double or triple bond, respectively, and include ethene, 3-butene, 2-ethenylbutene, isobutene, 1-pentene, 2-pentene, 1-hexene, 2-hexene, 1-octene, 3-octene, 1-decene, 1-dodecene, 1-tetradecene, 1-hexadecene, 1-octadecene, icos-2-ene and the like, and propyne, 2-butyne, 1-pentyne, 2-pentyne, 1-hexyne, 2-hexyne, 3-hexyne, 2-heptyne, 3-heptyne, 4-heptyne, 1-octyne, 2-octyne, 3-octyne, 4-octyne, 1-nonyne, 2-nonyne, 3-nonyne, 4-nonyne, 1-decyne, 2-decyne, 3-decyne, 4-decyne, 5-decyne, 1-dodecyne, 2-dodecyne, 3-dodecene, 4-dodecyne, 1-tetradecyne, 2-tetradecene, 4-tetradecene, 1-hexadecyne, 2-hexadecyne, 4-hexadecyne, 6-hexadecyne, 1-octadecyne, 2-octadecyne, 4-octadecyne, 6-octadecyne, 8-octadecyne, 9-octadecyne, icos-1-yne, icos-2-yne, icos-4-yne, icos-6-yne, icos-8-yne, and the like. Preferred are C2-C6 alkenes or C2-C6 alkynes, more preferably C2-C4 alkenes or C2-C4 alkynes, most preferably ethene, propene, acetylene or prop-1-yne. The term "C3-C20 cycloalkane" means a cyclic or bicyclic hydrocarbon having 3-20 carbon atoms such as cyclopropane, cyclobutane, cyclopentane, cyclohexane, cycloheptane, cyclooctane, cyclononane, cyclodecane, cycloundecane, cyclododecane, decalin, bicyclo[2.2.1]heptane also known as norbornane, and the like; and the term "C6-C14 monocyclic or polycyclic aromatic ring" denotes a carbocyclic aromatic molecule having 6-14 carbon atoms such as benzene, naphthalene and anthracene.

In certain embodiments, the hydrocarbon is a linear hydrocarbon as defined above, and the sulfonate that covers the nanoparticles is, in fact, a bolaamphiphile, also known as bolaform surfactant, bolaphile, or alpha-omega-type surfactant, i.e., an amphiphilic molecule having hydrophilic groups at both ends of a sufficiently long hydrophobic hydrocarbon chain.

In particular embodiments, the sulfonate protecting the nanoparticles comprised within the pharmaceutical composition of the invention is a moiety of an $\omega$-mercapto C2-C6 alkane sulfonate linked to the nanoparticle via the mercapto group. Non-limiting examples of such moieties include moieties of 2-mercaptoethane sulfonate, 3-mercaptopropane sulfonate, 4-mercaptobutane sulfonate, 5-mercaptopentane sulfonate and 6-mercaptohexane sulfonate, i.e., 2-sulfoethanethio, 3-sulfopropanethio, 4-sulfobutanethio, 5-sulfopentanethio and 6-sulfohexanethio, respectively. In more particular embodiments, the sulfonate protecting the nanoparticles comprised within the pharmaceutical composition of the invention is a moiety of 2-mercaptoethane sulfonate or 3-mercaptopropane sulfonate, preferably 2-mercaptoethane sulfonate.

In other particular embodiments, the sulfonate protecting the nanoparticles comprised within the pharmaceutical composition of the invention is a moiety of an ω-amino C2-C6 alkane sulfonate linked to the nanoparticle via the amino group. Non-limiting examples of such moieties include moieties of 2-aminoethane sulfonate, 3-aminopropane sulfonate, 4-aminobutane sulfonate, 5-aminopentane sulfonate and 6-aminohexane sulfonate, i.e., 2-sulfoethaneamino, 3-sulfopropaneamino, 4-sulfobutaneamino, 5-sulfopentaneamino and 6-sulfohexaneamino, respectively. In more particular embodiments, the sulfonate protecting the nanoparticles comprised within the pharmaceutical composition of the invention is a moiety of 2-aminoethane sulfonate or 3-aminopropane sulfonate.

In further particular embodiments, the sulfonate protecting the nanoparticles comprised within the pharmaceutical composition of the invention is a moiety of an ω-carboxy C2-C6 alkane sulfonate linked to the nanoparticle via the carbonyloxy group. Non-limiting examples of such moieties include moieties of 2-carboxyethane sulfonate, 3-carboxypropane sulfonate, 4-carboxybutane sulfonate, 5-carboxypentane sulfonate and 6-carboxyhexane sulfonate, i.e., 2-sulfoethanecarbonyloxy, 3-sulfopropanecarbonyloxy, 4-sulfobutanecarbonyloxy, 5-sulfopentanecarbonyloxy and 6-sulfohexanecarbonyloxy, respectively. In more particular embodiments, the sulfonate protecting the nanoparticles comprised within the pharmaceutical composition of the invention is a moiety of 2-carboxyethane sulfonate or 3-carboxypropane sulfonate.

The Examples hereinafter describe the synthesis of mercaptoethane sulfonate-protected water-soluble silver and gold nanoparticles (Ag-MES NPs and Au-MES NPs, respectively) based on the procedures described in Zou et al., 2006. As specifically shown, the Au-MES NPs had an average diameter of 4 nm, with a characteristic gold plasmon band at 519 nm seen by UV-visible spectroscopy absorption measurements. The peak seen by Fourier Transformed Infrared (FTIR) spectroscopy at 2561 cm-1 in pure sodium 2-mercaptoethanesulfonate (MESNA), correlating with the S—H stretching vibration modes, disappeared in the Au-MES NPs, indicating that MESNA binds to the gold core through the thiol group. On the other hand, the characteristic peaks of $SO_3^{2-}$ at 1045 and 1210 cm-1 seen with MESNA were present, indicating that the sulfonate functional group remains intact providing a negative charge and stability to the colloidal gold solution.

In certain particular embodiments, the pharmaceutical composition of the present invention thus comprises water-soluble 2-mercaptoethane sulfonate-protected nanoparticles as exemplified herein, i.e., water-soluble 2-mercaptoethane sulfonate-protected Ag nanoparticles or water-soluble 2-mercaptoethane sulfonate-protected Au nanoparticles, or a pharmaceutically acceptable salt thereof, and a pharmaceutically acceptable carrier.

The water-soluble sulfonate-protected metal, e.g., silver or gold, nanoparticles of the present invention may be synthesized by any suitable method or technology known in the art, e.g., as described in Zou et al., 2006, and in the Experimental hereinafter.

The pharmaceutical compositions of the present invention can be provided in a variety of formulations, e.g., in a pharmaceutically acceptable form and/or in a salt form, as well as in a variety of dosages.

In one embodiment, the pharmaceutical composition of the present invention comprises a non-toxic pharmaceutically acceptable salt of water-soluble sulfonate-protected nanoparticles as defined above, e.g., water-soluble sulfonate-protected metal or metal oxide nanoparticles.

Suitable pharmaceutically acceptable salts include salts of ammonium ($NH_4^+$) or an organic cation derived from an amine of the formula $R_4N^+$, wherein each one of the Rs independently is selected from H, C1-C22, preferably C1-C6 alkyl, such as methyl, ethyl, propyl, isopropyl, n-butyl, sec-butyl, isobutyl, tert-butyl, n-pentyl, 2,2-dimethylpropyl, n-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine. Additional suitable pharmaceutically acceptable salts may include metal salts of said water-soluble sulfonate-protected nanoparticles such as alkali metal salts, e.g., lithium, sodium or potassium salts, and alkaline earth metal salts, e.g., calcium or magnesium salts.

Further pharmaceutically acceptable salts of the water-soluble sulfonate-protected nanoparticles include salts of a cationic lipid or a mixture of cationic lipids. Cationic lipids are often mixed with neutral lipids prior to use as delivery agents. Neutral lipids include, but are not limited to, lecithins; phosphatidylethanolamine; diacyl phosphatidylethanolamines such as dioleoyl phosphatidylethanolamine, dipalmitoyl phosphatidylethanolamine, palmitoyloleoyl phosphatidylethanolamine and distearoyl phosphatidylethanolamine; phosphatidylcholine; diacyl phosphatidylcholines such as dioleoyl phosphatidylcholine, dipalmitoyl phosphatidylcholine, palmitoyloleoyl phosphatidylcholine and distearoyl phosphatidylcholine; phosphatidylglycerol; diacyl phosphatidylglycerols such as dioleoyl phosphatidylglycerol, dipalmitoyl phosphatidylglycerol and distearoyl phosphatidylglycerol; phosphatidylserine; diacyl phosphatidylserines such as dioleoyl- or dipalmitoyl phosphatidylserine; and diphosphatidylglycerols; fatty acid esters; glycerol esters; sphingolipids; cardiolipin; cerebrosides; ceramides; and mixtures thereof. Neutral lipids also include cholesterol and other 3β hydroxy-sterols.

Examples of cationic lipid compounds include, without being limited to, Lipofectin® (Life Technologies, Burlington, Ontario) (1:1 (w/w) formulation of the cationic lipid N-[1-(2,3-dioleyloxy)propyl]-N,N,N-trimethylammonium chloride and dioleoylphosphatidyl-ethanolamine); Lipofectamine™ (Life Technologies, Burlington, Ontario) (3:1 (w/w) formulation of polycationic lipid 2,3-dioleyloxy-N-[2 (spermine-carboxamido)ethyl]-N,N-dimethyl-1-propanamin-iumtrifluoroacetate and dioleoylphosphatidyl-ethanolamine), Lipofectamine Plus (Life Technologies, Burlington, Ontario) (Lipofectamine and Plus reagent), Lipofectamine 2000 (Life Technologies, Burlington, Ontario) (Cationic lipid), Effectene (Qiagen, Mississauga, Ontario) (Non liposomal lipid formulation), Metafectene (Biontex, Munich, Germany) (Polycationic lipid), Eu-fectins (Promega Biosciences, San Luis Obispo, Calif.) (ethanolic cationic lipids numbers 1 through 12: $C_{52}H_{106}N_6O_4.4CF_3CO_2H$, $C_{88}H_{178}N_8O_4S_2.4CF_3CO_2H$, $C_{40}H_{84}NO_3P.CF_3CO_2H$, $C_{50}H_{103}N_7O_3.4CF_3CO_2H$, $C_{55}H_{116}N_8O_2.6CF_3CO_2H$, $C_{49}H_{102}N_6O_3.4CF_3CO_2H$, $C_{44}H_{89}N_5O_3.2CF_3CO_2H$, $C_{100}H_{206}N_{12}O_4S_2.8CF_3CO_2H$, C162H330N22O9.13CF3CO2H, C43H88N4O2.2CF3CO2H, C43H88N4O3.2CF3CO2H, C41H78NO8P); Cytofectene (Bio-Rad, Hercules, Calif.) (mixture of a cationic lipid and a neutral lipid), GenePORTER® (Gene Therapy Systems, San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

The pharmaceutically acceptable salts of the present invention may be formed by conventional means, e.g., by reacting a free acidic form of the active agent or ingredient, i.e., the water-soluble sulfonate-protected nanoparticles, with one or more equivalents of the appropriate base in a solvent or medium in which the salt is insoluble, or in a solvent such as water which is removed in vacuo or by freeze drying, or by exchanging the cation of an existing salt for another cation on a suitable ion exchange resin.

The pharmaceutical compositions provided by the present invention may be prepared by conventional techniques, e.g., as described in Remington: The Science and Practice of Pharmacy, 19th Ed., 1995. The compositions can be prepared, e.g., by uniformly and intimately bringing the active agent, i.e., the water-soluble sulfonate-protected nanoparticles, into association with a liquid carrier, a finely divided solid carrier, or both, and then, if necessary, shaping the product into the desired formulation. The compositions may be in solid, semi-solid or liquid form and may further include pharmaceutically acceptable fillers, carriers, diluents or adjuvants, and other inert ingredients and excipients. The compositions can be formulated for any suitable route of administration, e.g., oral, nasogastric, nasoenteric, orogastric, parenteral (e.g., intramuscular, subcutaneous, intraperitoneal, intravenous, or intraarterial injection, or implant), gavage, buccal, nasal, sublingual or topical administration, as well as for inhalation. The dosage will depend on the state of the patient, and will be determined as deemed appropriate by the practitioner.

Particular pharmaceutical compositions according to the invention may comprise the active agent formulated for controlled release in microencapsulated dosage form, in which small droplets of the active agent are surrounded by a coating or a membrane to form particles in the range of a few micrometers to a few millimeters, or in controlled-release matrix. Other pharmaceutical compositions may comprise the active agent formulated as a depot system based on biodegradable polymer or a mixture of the same or different biodegradable polymers, wherein as the polymer(s) degrades, the active agent is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

In certain embodiments, the pharmaceutical composition of the present invention is formulated for topical administration. According to the present invention, pharmaceutical compositions for topical application may be formulated as an aqueous solution, a gel, a cream, a paste, a lotion, a spray, a suspension, a dispersion, a salve or an ointment. In one embodiment, the pharmaceutical composition further comprises a solid support for prolonged release of the active ingredient, i.e., the water-soluble sulfonate-protected nanoparticles.

The pharmaceutical composition of the invention may be in a form suitable for oral use, e.g., as tablets, troches, lozenges, aqueous, or oily suspensions, dispersible powders or granules, emulsions, hard or soft capsules, or syrups or elixirs. Compositions formulated for oral administration may be prepared according to any method known in the art and may further comprise one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in U.S. Pat. Nos. 4,256,108, 4,166,452 and 4,265,874 (each incorporated by reference herein in its entirety) to form osmotic therapeutic tablets for control release. In particular embodiments, the pharmaceutical composition is formulated in a suitable form, e.g., tablets such as matrix tablets, in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity.

The pharmaceutical composition of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

The pharmaceutical compositions of the invention may also be in a form suitable for inhalation. Such compositions may be administered using any suitable device known in the art such as metered dose inhalers, liquid nebulizers, dry powder inhalers, sprayers, thermal vaporizers, electrohydrodynamic aerosolizers, and the like.

The present invention provides a novel approach for the inhibition of infections caused by microorganisms capable of binding to heparan sulfate, such as the herpes simplex virus-1 (HSV-1), using water-soluble anionic nanoparticles, e.g., silver and gold nanoparticles, to which multiple functionalized groups, more specifically sulfonate-containing groups, are linked through thiol, amino or carboxyl groups. The sulfonate-containing groups protecting said nanoparticles interact with the virus by multivalent bonds thereby blocking attachment and penetration of the virus into the cells, and also cell-to-cell spread of the virus.

As shown in Example 1 hereinafter, Ag-MES NPs are capable of inhibiting plaque formation in Vero cells infected with HSV-1 virus without affecting cell viability. Example 3 also shows that Vero cells infected with HSV-1 in the presence of Au-MES NPs show little or no plaque formation, as opposed to cells infected with virus in the absence of Au-MES NPs. Additional studies pertaining to the mechanism, as shown in Example 5, revealed attachment and penetration blockage of the virus infection of the cells. Furthermore, cell-to-cell spread inhibition as a mode of virus inactivation was also observed. Taken together, these results indicate that Au-MES NPs and likely also Ag-MES NPs inhibit HSV-1 infections by blocking the attachment and thereby the entrance of the virus into the cells and/or by preventing the cell-to-cell spread of the virus, suggesting a comprehensive viral inhibition achieved by the Au-MES NPs and Ag-MES NPs. Importantly, Ag-MES NPs and Au-MES NPs were also found not to be toxic to the cells.

In certain embodiments, the pharmaceutical composition of the present invention, as defined above, is thus used for prevention or treatment of an infection, condition or disorder caused by a microorganism capable of binding to heparan sulfate. In particular embodiments, said infection, condition or disorder is either prevented or treated, or has symptoms that are prevented or treated, by topical administration of said pharmaceutical composition. In certain specific embodiments, said microorganism capable of binding to heparan sulfate is a virus such as a member of the herpesviridae family, the papillomavirus family, or the flaviviruses family, or is human immunodeficiency virus (HIV), more specifically, a member of the herpesviridae family, e.g., HSV-1 or herpes simplex virus-2 (HSV-2). In other specific embodiments, said microorganism capable of binding to heparan sulfate is a bacterium such as *Helicobacter Pylori, Staphylococcus Aureus*, a *Streptococcus* of group A, or a mycobacterium such as *Mycobacterium leprae*.

The infection, condition or disorder caused by the microorganism capable of binding to heparan sulfate, as defined above, may be either mucocutaneous or non-mucocutaneous infection, condition or disorder. The term "mucocutaneous infection, condition or disorder", as used herein, refers to an infection, condition or disorder at a mucocutaneous zone, i.e., a region of the animal body in which mucosa transitions to skin, more particularly, a body orifice. In humans, mucocutaneous zones are found at the lips, nostrils, conjunctivae, urethra, vagina and anus. Examples of such mucocutaneous infections, conditions or disorders include, without being limited to, mucocutaneous infections, conditions or disorders caused by HSV such as labial herpes, keratitis, or genital herpes; and mucocutaneous infection, conditions or disorders caused by human papillomavirus such as genital warts, or vaginal cancer. Non-limiting examples of such non-mucocutaneous infections, conditions or disorders include infections, conditions or disorders caused by human papillomavirus such as cervical cancer or skin warts (verrucae); infections, conditions or disorders caused by *Helicobacter Pylori* such as duodenal and gastric ulcers or stomach cancer; infections, conditions or disorders caused by *Mycobacterium leprae* such as Leprosy; and infections, conditions or disorders caused by *Staphylococcus Aureus* or by a group A Streptococci, such as necrotizing fasciitis.

In another aspect, the present invention relates to a method for prevention or treatment of an infection, condition or disorder caused by a microorganism capable of binding to heparan sulfate in an individual in need, said method comprising administering to said individual a prophylactically or therapeutically effective amount of a pharmaceutical composition comprising water-soluble sulfonate-protected nanoparticles or a pharmaceutically acceptable salt thereof.

The term "treatment" as used herein with respect to an infection, condition or disorder caused by a microorganism capable of binding to heparan sulfate refers to administration of a pharmaceutical composition according to the present invention after the onset of symptoms of said infection, condition or disorder. The term "prevention" as used herein with respect to an infection, condition or disorder caused by a microorganism capable of binding to heparan sulfate refers to administration of said pharmaceutical composition prior to the onset of symptoms of said infection, condition or disorder. The terms "prophylactically effective amount" and "therapeutically effective amount" as used herein refer to the quantity of the pharmaceutical composition as defined above that is useful to prevent or treat an infection, condition or disorder caused by a microorganism capable of binding to heparan sulfate.

The invention will now be illustrated by the following non-limiting Examples.

EXAMPLES

Experimental

Synthesis of silver nanoparticles stabilized by mercaptoethanesulfonate (Ag-MES NPs): Ag-MES NPs were synthesized as described in Baram-Pinto et al., 2009. In particular, Ag-MES NPs were synthesized by a modified procedure with a sonochemical reaction based on that described by Zou et al., 2006. $AgNO_3$ in ethanol was mixed with sodium 2-mercaptoethane sulfonate (MES, Fluka Analytical) dissolved in 25 ml of ethanol and 25 ml of a double-distilled water (DDW) solution. After purging the reaction mixture with argon gas for 30 min, sonochemical irradiation (Ti horn from Sonics and Materials VCX 600, 20 kHz, 600 W at 60% efficiency) was applied for 15 min in argon atmosphere. $NH_3$ (0.1 ml, 25%) was injected into the flask 4 min after the start of the sonication. The reaction was held at a 10° C., using a water-ice bath.

Characterization of Ag-MES NPs: The morphology of the nanostructures was characterized with a Philips CM-120 transmission electron microscope (TEM), operating at 120 kV. Images were recorded by a Gatan Ultrascan 1000 2 k×2 k CCD camera. The nanoparticle size distribution was further characterized using Scion Image software (Alpha 4.0.3.2) based on the TEM images. X-ray photoelectron spectroscopy (XPS) was performed using an Axis HS with monochromatic Al KR source (Kratos Analytical). Thermogravimetric analysis (TGA) measurements were conducted using a TGA model Q500 (TA Instruments), equipped with a Pt crucible, for the estimation of the amount of the MES surfactant on the surface of the silver nanoparticles.

Synthesis of gold nanoparticles stabilized by mercaptoethanesulfonate (Au-MES NPs) and bare Au NPs: Au-MES NPs were synthesized using a solution-based method as described in Zou et al., 2006. More particularly, to aqueous $HAuCl_4$ solution (150 ml, 1 mM), aqueous solution of sodium 2-mercaptoethanesulfonate (MESNA) (50 ml, 9 mM) was added under vigorous stirring. Aqueous $NaBH_4$ (10 ml, 0.01 g) was immediately added to the above solution and the stirring was continued for 1 hour. The solution turned light brown with the addition of $NaBH_4$. Additional $NaBH_4$ (0.04 g, 5 ml) was added after 1 hour resulting in dark brown coloration of the solution. The reaction was continued overnight to reach completion. After the synthesis, the Au-MES NPs solution was dialyzed against deionized water for 24 h in a 12.5 kDa dialysis membrane, with intermittent change of water. The dialysis assisted in the removal of free MESNA and unreduced chloroaurate ions. Purified Au-MES NPs solution was then lyophilized for a period of two days to obtain dry powder which was readily redispersible in water.

Unmodified gold nanoparticles (Au NPs) were synthesized as previously described (Patil et al., *Langmuir*, 1999, 15, 8197-8206; incorporated by reference herein in its entirety). Briefly, to aqueous HAuCl4 solution (90 ml of 0.1 mM), NaBH4 (10 ml of 0.1 g) was added with rapid stirring resulting in wine red coloration. The reaction was continued overnight after which the solution was purified by dialysis and lyophilized as described earlier.

Characterization of Au-MES NPs: High Resolution Transmission Electron Microscopy (HRTEM) measurements were carried out on a 200 KV JEOL, JEM 2100 instrument with a resolution of 0.1 nm. The samples were prepared by drop-coating nanoparticle solution on copper grids and allowing it to air dry. Ultraviolet-visible spectroscopy (UV-vis) absorption measurements of Au-MES NPs solution were carried out on a Cary 100 Scan UV spectrophotometer, while Fourier Transformed Infrared (FTIR) spectroscopy analysis of pure MESNA and Au-MES NPs taken in KBr pellets was carried out on a Nicolet 400D Impact FTIR instrument over a range of 400-4000 cm-1. Z potential measurements were recorded on a Malvern Zetasizer 3000 HSA.

Cell culture and toxicity assays: The cytotoxicity was examined using a cell proliferation kit with an XTT (2,3-bis (2-methoxy-4-nitro-5-sulfophenyl)-5-[(phenylamino)carbonyl]-2H-tetrazolium hydroxide)-based colorimetric assay that measures mitochondrial activity (Biological Industries), according to the manufacturer's instructions. Optical density (OD) measurements for calculating cell viability percentage were taken using a TECAN Spectrafluor Plus (NEOTEC Scientific Instrumentation Ltd.) spectrophotometer at a wavelength of 405 nm. Vero cell monolayers were grown in 96-well plates (2.5×10-4 cells/well) in Minimal Essential Medium (MEM)-Eagle supplemented with 5% FCS heat-inactivated fetal calf serum (FCS), L-glutamine and Penicillin-Streptomycin-Amphotericin (PSA). Cells were maintained at 37° C. under 5% CO2. Ag- or Au-MES NPs were added into each well at different concentrations (25-800 µg/ml or 50-1000 µg/ml, respectively, in a total volume of 150 µl/well). The control consisted of Vero cell monolayers with no nanoparticles. Additional controls, to take into account the optical absorbance of the nanoparticles, consisted of equivalent concentration of nanoparticles suspended in MEM and FCS. The OD measurements of these solutions were subtracted from the experimental values.

Antiviral assay: The virus used was the wild-type HSV-1 McIntyre strain. For the inhibition experiments, 7×104 Vero cells/well were grown in 24 well plates. Infection was carried out by adding 250 µl of virus suspensions with or without the Ag- or Au-MES NPs to the cells followed by 45 min incubation. Thereafter, the cells were overlaid with solutions containing 2% serum and 0.1% human γ-globulin (final concentrations) with or without Ag- or Au-MES NPs, to maintain constant nanoparticles concentrations.

End point assay: For the end point assay, 7×104 Vero cells/well were grown on a 24-well plate. Cells were then infected with 250 µl of virus solution to obtain a multiplicity of infection (MOI) of 20 (1.5×106 plaque forming units (PFU)) or 70 (5×106 PFU) without human γ-globulin to allow full infection of the virus with minimum interventions in the presence and absence of Au-MES NPs. The plates were incubated at 37° C. for 45 minutes, and 500 µl of MEM-Eagle with 2% serum was then added. After 24 hours, the cells and media were collected and stored at −80° C. Fresh cell cultures were grown on 24-well plates (7×104 cells/well) and infected with the virus suspensions for titration of the samples using a standard plaque assay.

Time point assay: Vero cells were infected with a viral load of 150 PFU/well and incubated for 45 minutes at 37° C. Then, the cell cultures were washed and overlaid with fresh media containing 0.1% of human γ-globulin. The medium was replaced with Au-MES NPs solution at 400 µg/ml with 2% FCS and 0.1% human γ-globulin after 1, 12 and 24 hours. Plaque sizes were measured using AxioVision software release 4.7.2 and averaged for 100 plaques in each set, 48 hours post infection.

Cell pretreatment with Au-MES NPs: Vero cell cultures were preincubated with 400 µg/ml of Au-MES NPs for 24 hours at 37° C., and were then washed and infected with 750 µl of HSV-1 virus suspension (600 PFU/well), and subsequently overlaid with medium containing 2% FCS and 0.1% human γ-globulin. For comparison, a similar treatment was performed with cell cultures that were not treated with Au-MES NPs. The number and size of the plaques were measured 48 hours following infection.

Example 1

Mercaptoethane Sulfonate-Protected Water-Soluble Silver Nanoparticles Inhibit HSV-1 Infectivity and do not Affect Cell Viability In a preliminary study, mercaptoethane sulfonate-protected water-soluble silver nanoparticles (Ag-MES NPs) were synthesized as described in the Experimental, and the nanoparticles were almost uniformly distributed with particle size varying from 3-4 nm. The toxicity of the Ag-MES NPs to Vero cells was examined using a cell proliferation kit with an XTT-based colorimetric assay, as described in the Experimental. No effect on the mitochondrial activity of the cell was observed with these particles at concentrations up to 0.8 mg/ml. The capacity of these particles to inhibit HSV-1 infectivity was determined as described in the antiviral assay in the Experimental. Briefly, Vero cell monolayers were infected with HSV-1 in the presence or absence of nanoparticles and observed for the presence of plaques after 48 hours. As shown in FIG. 1, the infection with HSV-1 was almost completely blocked in the presence of the particles, indicating that sulfonate-protected nanoparticles such as Ag-MES NPs have an inhibitory effect on HSV-1 and can thus be used for the treatment of HSV-1 infection. Furthermore, these nanoparticles may afford topical treatment for genital infections.

Example 2

Characterization of Au-MES NPs

Figure 2A:
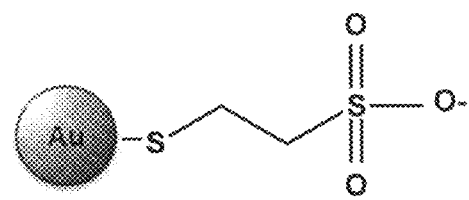
FIGS. 2A-2E show characterization of mercaptoethane sulfonate-protected gold nanoparticles (Au-MES NPs). Schematic representation of Au-MES NPs (2A); Representative high resolution transmission electron microscopy (HR-TEM) images of Au-MES NPs, at two different scales (2B and 2C); Ultraviolet visible spectroscopy (UV-Vis) absorption spectrum of Au-MES NPs over a wavelength range of 400-800 nm (2D); and Fourier Transformed Infrared (FTIR) spectra over a range of 400-4000 $cm^{-1}$ of MESNA (upper track) and Au-MES NPs (lower track) (2E). a.u.—arbitrary units; *—S—H vibration mode.
Figure 2B:
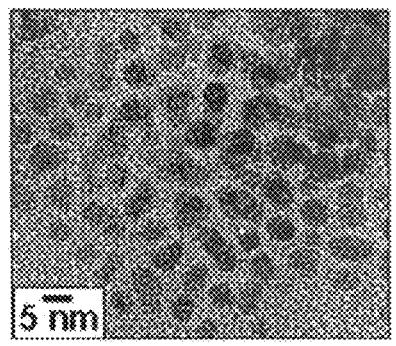
Figure 2C:
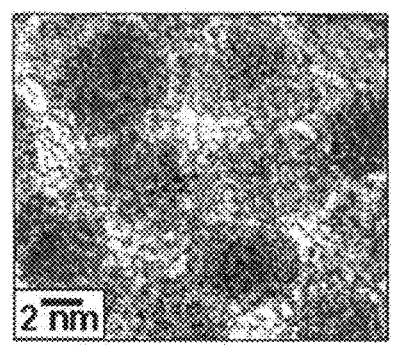
Figure 2D:
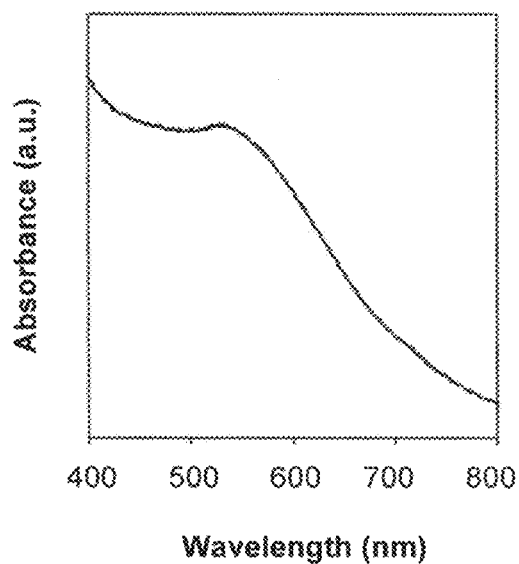
Figure 2E:
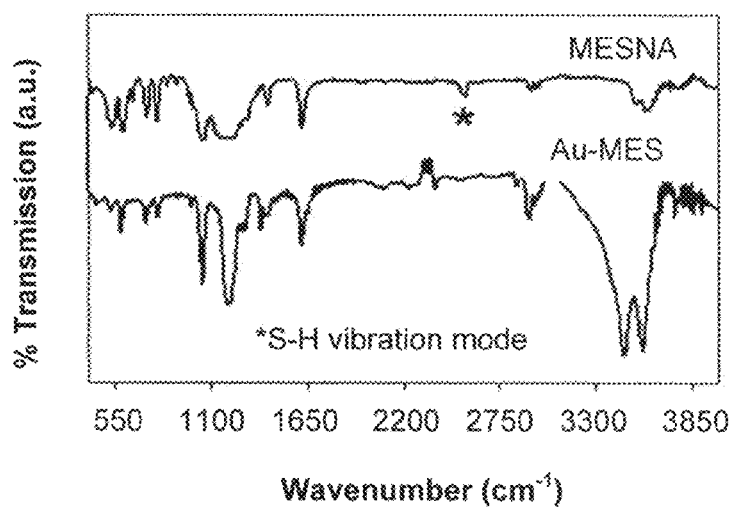

Au-MES NPs, schematically illustrated in FIG. 2A, were synthesized as described in Experimental. High Resolution Transmission Electron Microscopy (HRTEM) measurements revealed that the Au-MES NPs synthesized had an average diameter of 4 nm (FIGS. 2B and 2C). UV-vis absorption measurements of Au-MES NPs solution showed a characteristic gold plasmon band at 519 nm (FIG. 2D). Fourier Transformed Infrared (FTIR) spectroscopy analysis of pure mercaptoethanesulfonate (MESNA) and Au-MES NPs was carried out over a range of 400-4000 cm-1 (FIG. 2E). The spectrum corresponding to pure MESNA showed a peak at 2561 cm-1 which correlates to the S—H stretching vibration modes (Silverstein et al., in *Spectrometric Identification of Organic Compounds*. 5th Ed.; Wiley: New York, 1991; Zou et al., 2006; each incorporated by reference herein in its entirety); however, this peak disappeared in the spectrum corresponding to Au-MES NPs, indicating that MESNA binds to the gold core through the thiol group. The characteristic peaks of SO32- at 1045 and 1210 cm-1 (Silverstein et al., 1991) were present in both spectra suggesting that the sulfonate functional group remains intact providing a negative charge and stability to the colloidal gold solution (zeta potential: −32 mV). The broad signal at 3500 cm-1 is attributed to the symmetric and antisymmetric vibration of O—H functional group in water (Silverstein et al., 1991).

Example 3

Antiviral Activity of Au-MES NPs Against HSV-1

Figure 3A:
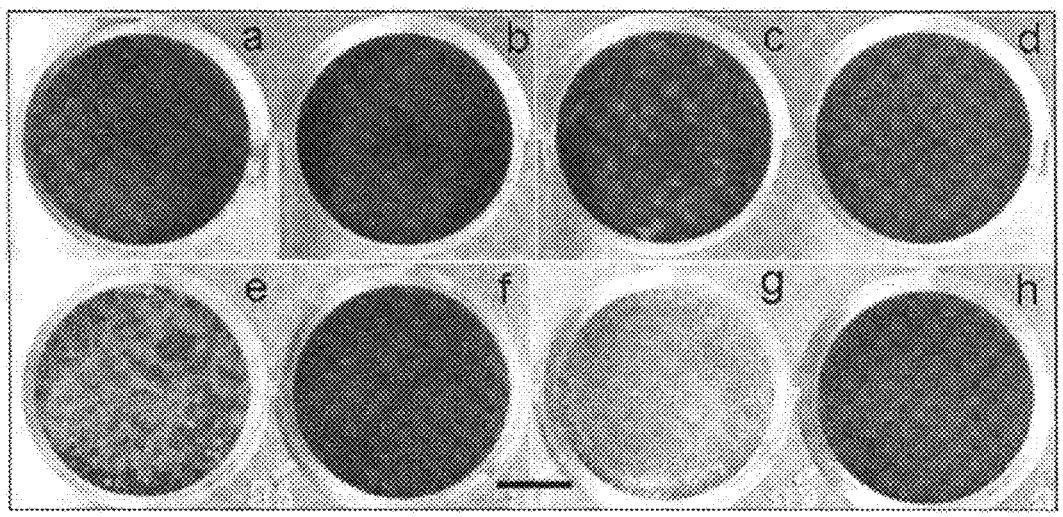
FIGS. 3A-3B show plaque reduction assay using Vero cell cultures infected with HSV-1 in the presence and absence of Au-MES NPs (3A) and plaque reduction assay for antiviral activity of soluble MES (3B). Pictures were taken 48 hours following infection. 3A shows mock-infected cell cultures (panel a); mock-infected cells treated with 400 μg/ml Au-MES NPs (panel b); cells infected with increasing viral loads (42, 420 or 4200 PFU, respectively) (panels c, e and g); and cells infected with increasing viral loads (42, 420 or 4200 PFU, respectively) in the presence of 400 μg/ml Au-MES NPs (panels d, f and h). 3B shows uninfected cell cultures treated with 50, 100, 200, 400, 800 or 1000 μg/ml soluble MES, respectively (panels a, c, e, g, i and k); and the corresponding infected cell cultures (infected with 80 PFU), treated at the same concentrations (panels b, d, f, h, j and l). Scale bars correspond to 5 mm.

In order to evaluate the antiviral activity of the Au-MES NPs, a plaque reduction assay was used. Cell monolayers were infected with HSV-1 in the presence or absence of the nanoparticles, as described in the antiviral assay in the Experimental, and observed for the presence of plaques after 48 hours. Plaque formation was obtained by the addition of γ-globulins, which prevents virus dissemination while retaining cell-to-cell spread. FIG. 3A (panels a-h) show images of the cell cultures after 48 hours. As shown, mock infected cells either not treated (panel a) or treated with Au-MES NPs (panel b) showed similar monolayer morphology and viability. Infected cell cultures that were not treated with Au-MES NPs showed typical cytopathic effect resulting in distinct plaques. Large plaques were observed at 42-plaque forming unit (PFU) (panel c) and 420-PFU (panel e), while massive cell destruction was observed at 4200-PFU (panel g). In contrast, infected cell cultures treated with Au-MES NPs at all viral loads remained similar to the mock infected cell cultures, illustrating the inhibitory activity of the nanoparticles (panels d, f & h).

In the second experiment, the antiviral activity of the nanoparticles was further assessed using an end-point experiment. Cells were infected with HSV-1 at multiplicity of infection (MOI) of 20 or 70 without human γ-globulin to allow full infection of the virus with minimum interventions, in the presence and absence of Au-MES NPs. After 24 hours, the cells and media were collected and kept at −80° C. Fresh cell cultures were grown and infected with the virus suspensions for titration of the samples. While in control sets with initial viral infection in the absence of Au-MES NPs, a concentration of $5 \times 10^4$ PFU/ml was determined, no plaques appeared in the cell cultures inoculated with extracts of cells initially infected with viruses in the presence of nanoparticles (data not shown), indicating that the Au-MES NPs completely blocked the viral infection and providing further demonstration to the efficient inhibitory effect of the Au-MES NPs on HSV-1.

Figure 3B:
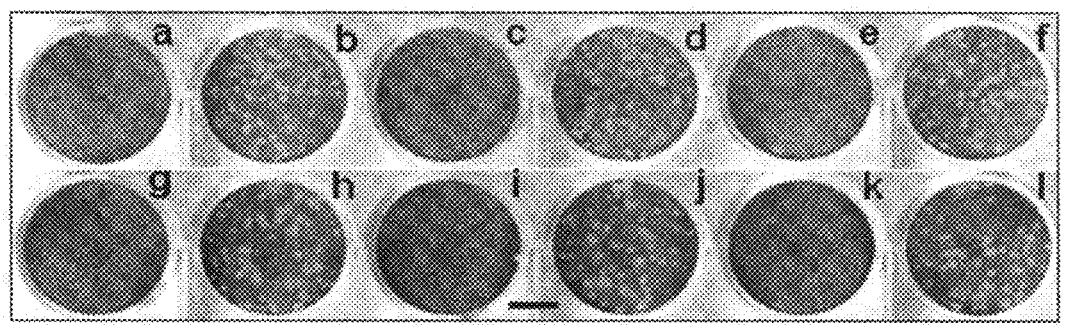

For comparison, the effect of soluble MES was examined under similar experimental conditions using various MES concentrations (50-1000 μg/ml) representing higher amount of MES than present in the Au-MES NPs used in the experiments described above. As shown in FIG. 3B, soluble MES was found to be completely ineffective in inhibiting the virus infection in terms of number of plaques and their average size at all tested concentrations. Similarly, in another control experiment, equivalent amounts of unmodified gold nanoparticles (Au NPs) were tested for anti HSV-1 activity using a plaque reduction assay. Results in terms of plaque numbers and size revealed the inability of the gold nanoparticles to inhibit HSV-1 infection (data not shown). These control experiments suggest that the antiviral activity of the Au-MES NPs is due to the MES functional groups linked to the gold nanoparticle surfaces, rather than the unmodified gold nanoparticles or the MES per se.

Example 4

Cytotoxicity of Au-MES NPs

Figure 4:
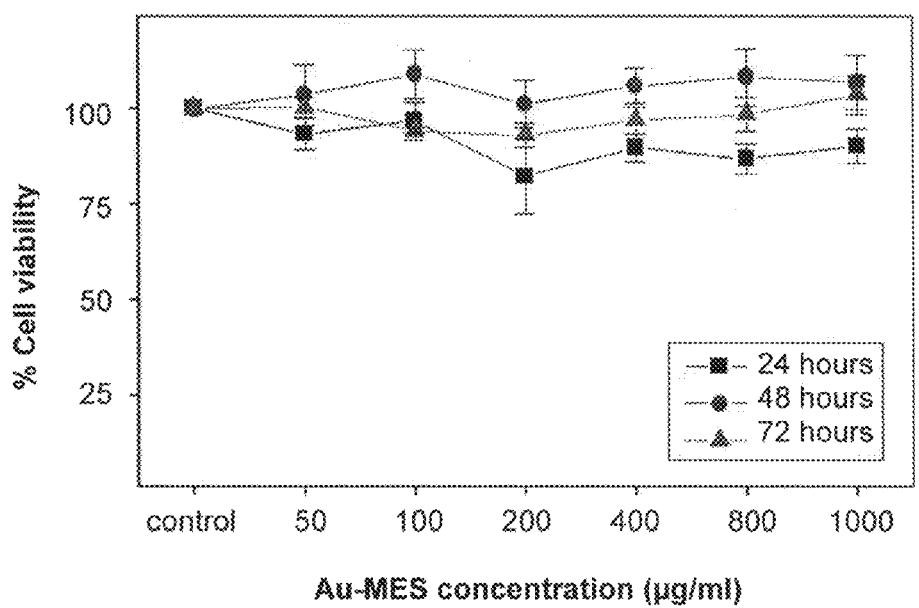
FIG. 4 shows the effect of Au-MES NPs on the viability of kidney epithelial Vero host cells. Vero cell monolayers were grown in 96-well plates ($2.5 \times 10^{-4}$ cells/well) with 5% FCS in MEM-Eagle. Au-MES NPs were added into each well at different concentrations (50-1000 μg/ml at a total volume of 150 μl/well), and Vero cell monolayers with no Au-MES NPs served as a control. XTT measurements were carried 24 (squares), 48 (circles) and 72 (triangles) hours after the addition of Au-MES NPs, and the results are presented as the percentage of viable cells relative to control cultures. Similar results were obtained in two additional independent experiments.

Since viruses reproduce only in host cells (Murray et al., in *Medical microbiology.* $3^{rd}$ ed.; Mosby: St. Louis, Mo., 1998; incorporated by reference herein in its entirety), it was essential to examine the toxicity of the Au-MES NPs on the kidney epithelial Vero host cells used in our study for HSV-1 infections. The cytotoxicity was examined using the XTT cell viability assay as described in Experimental. As shown in FIG. 4, demonstrating the results calculated as the percentage of viable cells relative to control cultures, cell viability was maintained close to 100% at all tested conditions.

Example 5

The Mechanism of HSV-1 Viral Inhibition by Au-MES NPs

There are three possible mechanisms that could explain the inhibition of virus infection by the Au-MES NPs: Inhibition of the attachment of the virus to the cell, inhibition of cell-to-cell viral spread, and alteration of cell susceptibility to viral infection induced by the nanoparticles present in the media or within the cells. Since such mechanisms could be accounted, independently or in combination, for generating the antiviral effects, a set of experiments was carried out trying to determine the exact anti-viral mechanism of these nanoparticles.

Inhibition of Plaque Formation

Figure 5:
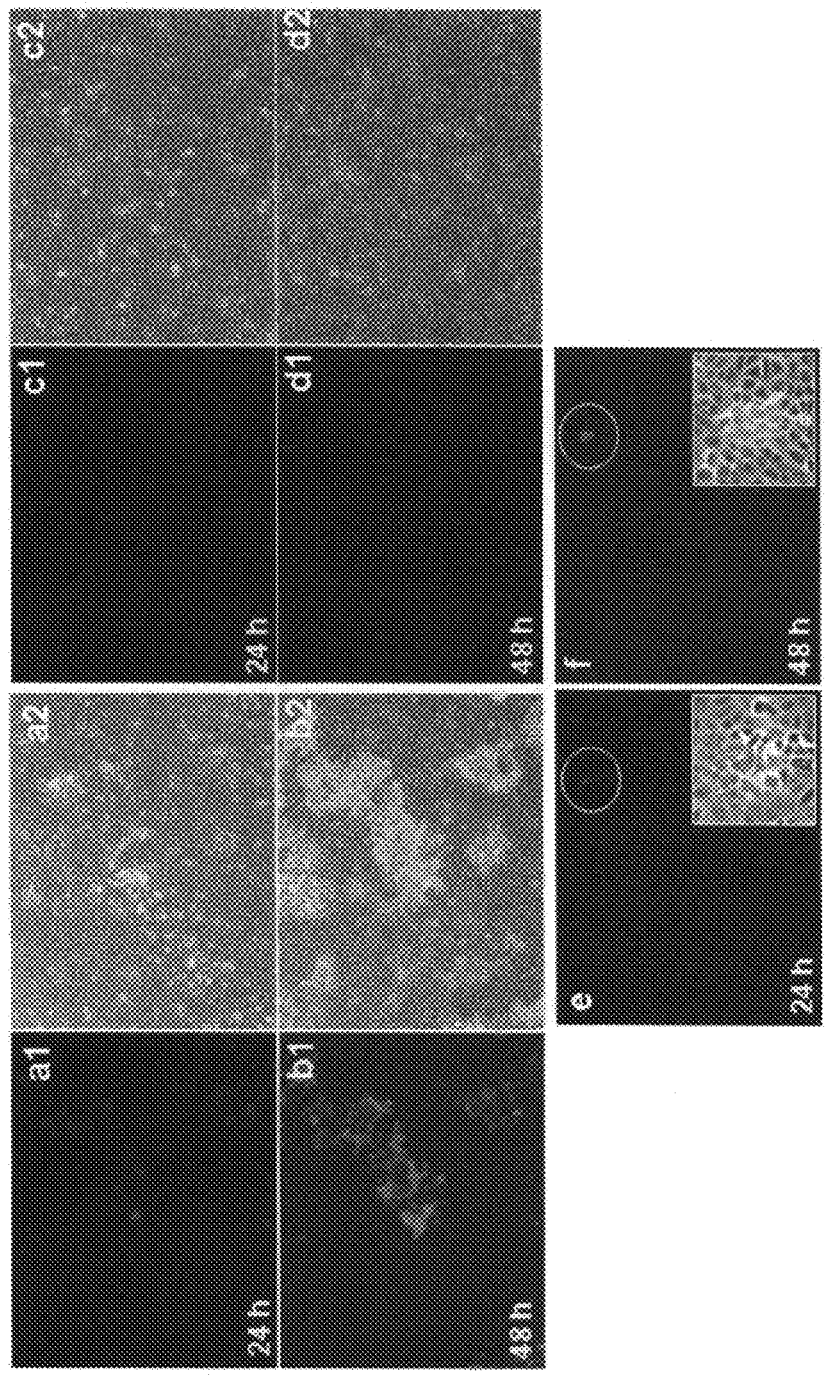
FIG. 5 shows live imaging fluorescence microscopy of Vero cells infected with GFP-expressing HSV-1. Images captured from cells infected in absence (panels a1, a2, b1, b2) or presence (panels c1, c2, d1, d2) of Au-MES NPs 24 hours (panels a1, a2 and c1, c2) and 48 hours (panels b1, b2 and d1, d2) post infection. Panels e and f show a rare infection observed in the presence of Au-MES NPs after 24 hours or 48 hours, respectively. Inset shows the circled area in the corresponding fluorescence microscopy images. Panels a1, b1, c1, d1, e and f are fluorescence microscopy images, panels a2, b2, c2 and d2 are differential interference contrast images merged with the corresponding fluorescence images.

First, we used live imaging microscopy (Axio Observer Z1, Zeiss equipped with Hamamatsu, OCRA-ER camera) using the recombinant HSV-1 strain 17+20.5/5 that contains a green fluorescence protein (GFP) expression cassette. Cells infected with this virus produce GFP, enabling monitoring of the virus spread in the cell culture in real time. FIG. 5 shows the appearance of plaques 24 hours post-infection in cells that were not treated with Au-MES NPs (panels a1 and a2), and further time-lapse imaging revealed massive viral spread to neighboring cells after 48 hours, with large plaques and many green cells (panels b1 and b2). In contrast, in the presence of Au-MES NPs, neither plaques nor GFP labels were observed after 24 h (panels c1, c2) or 48 h (panels d1, d2). These findings are in agreement with our previous plaque reduction observations and further suggest that the inhibition mechanism is generic and not HSV-1 strain dependent.

Inhibition of Cell-to-Cell Viral Spread

In very few cases, however, where infected cells were noticed, use of GFP-positive HSV-1 allowed the monitoring of cell-to-cell spread. As evident in FIG. 5 panels E and F, the cell-to-cell spread of the virus was restricted to a small number of neighboring cells (~six adjacent cells), as compared to the large scale spread of the infection in the absence of Au-MES NPs. These results clearly demonstrate the inhibition of cell-to-cell spread of HSV-1 by the Au-MES NPs. We believe this is a result of the ability of nanoparticles to enter the intercellular spaces while maintaining their potency to inhibit fusion events between the plasma membranes of infected and uninfected cells.

Figure 6A:
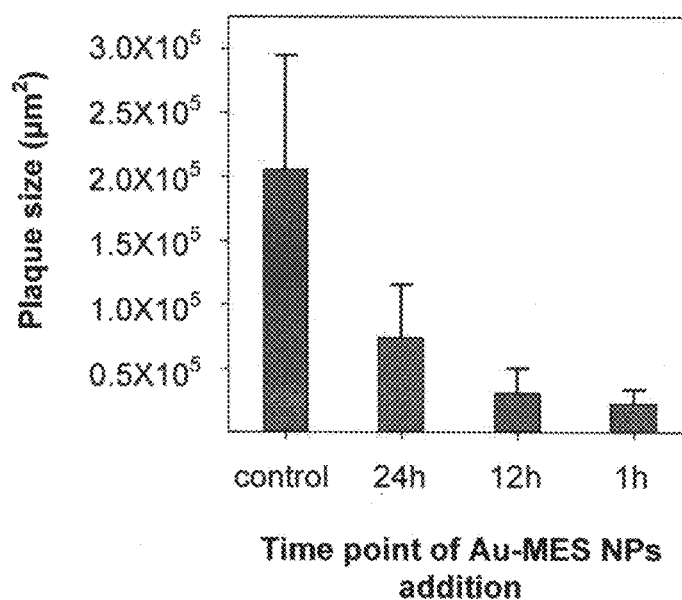
FIGS. 6A-6D show inhibition of plaque formation, cell-to-cell viral spread and virus attachment by Au-MES NPs. Variation of plaque size ($\mu m^2$) as a function of increasing time lapse (1, 12 and 24 hours) between primary infection and the administration of Au-MES NPs. control—without Au-MES NPs (6A); Evaluation of inhibition of virus entry into host cells. Number of PFU observed 48 hours post infection without (1) and with (2) nanoparticles. Inset shows a light microscopy image of the corresponding cell cultures. Scale bar corresponds to 10 mm (6B); Blockage of virus attachment to the host cells: cell culture infected in the absence (6C) or presence (6D) of Au-MES NPs. Scale bar corresponds to 200

In order to further validate the inhibition of cell-to-cell viral spread, an experiment was carried out by infecting the cell cultures with the virus and then adding the Au-MES NPs at different time points following infection, as described in the time point assay in Experimental. Such an experiment allows onset of the primary virus infection and examines the ability of the Au-MES NPs to inhibit the infectious cycle at the stage of cell-to-cell spread. Cells were infected with HSV-1 and incubated for 45 minutes. Then, the cell cultures were washed and overlaid with fresh media containing human γ-globulin. This enabled a primary viral infection, but at the same time, prevented the possibility of delayed infection from the remaining viruses in the culture media. Therefore, it synchronized the experimental conditions in terms of the number of virions in the system and the time of infection, to allow comparison of plaque sizes between the different treatments. Furthermore, although free viruses released to the media are inactivated in the presence of human γ-globulin, direct cell-to-cell spread of infection is expected to persist. Thereafter, the medium was replaced with a medium containing Au-MES NPs at different time points. FIG. 6A shows the variation in plaque area (in μm2) as a function of time of Au-MES NPs addition post infection. Large plaques (average size: $20.58 \times 10^4 \pm 8.8 \times 10^4$ μm2) appeared in control cell cultures that were not treated with Au-MES NPs. However, when nanoparticles were added, relatively smaller plaques were observed depending on the time lapse between the infection and administration of Au-MES NPs. Thus, addition of particles after 1 hour of infection led to the smallest plaque size (average $2.26 \times 10^4 \pm 1 \times 10^4$ μm2), whereas the plaque size increased with further delay in addition of Au-MES NPs (12 hours: $3.13 \times 10^4 \pm 1.8 \times 10^4$ μm2; 24 hours: $7.46 \times 10^4 \pm 4 \times 10^4$ μm2). Consequently, the plaque sizes varied as a function of the time of Au-MES NPs administration, and corresponded to the inhibition of cell-to-cell spread of the virus by the nanoparticles, indicating that even at a later stage of infection, the Au-MES NPs were effective in controlling viral spread.

Inhibition of Virus Penetration into Cells

Figure 6B:
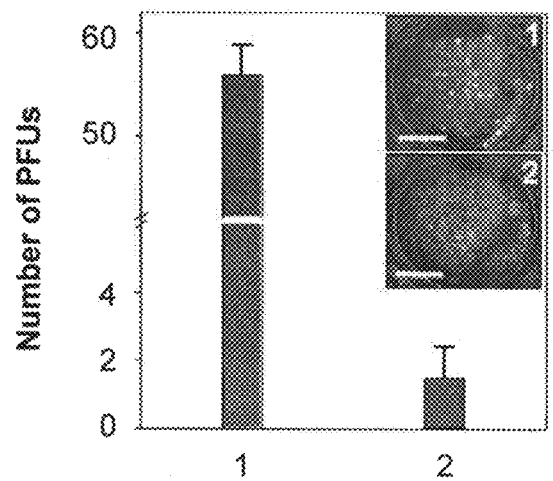

In order to further examine the inhibition mechanism, we carried out an experiment to evaluate the effect of the nanoparticles on the penetration of the virus into the cells, by segregating this stage from cell-to-cell spread. Cells were infected with HSV-1 in the presence or absence of Au-MES NPs and incubated for 2 hours to allow attachment and penetration of the virus into the cells. Cells were then washed and overlaid with fresh media lacking Au-MES NPs and containing human γ-globulin. The subsequent washing ruled out infection by unadsorbed virions, but cell-to-cell spread was expected to continue, resulting in plaques. As shown in FIG. 6B, cells treated with Au-MES NPs showed a significantly lower number of plaques after the washing (2±1) as compared to cells not treated with Au-MES NPs (56±3), suggesting that inhibition of virus infection by the nanoparticles prevented entry of the virus, as there were no Au-MES NPs later on to stop the cell-to-cell spread.

Figure 6C:
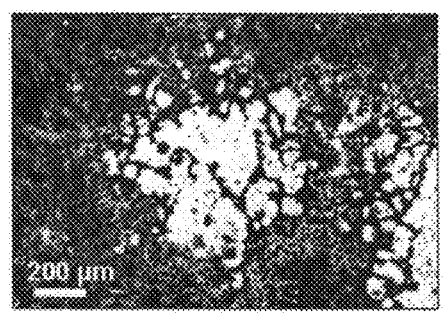
Figure 6D:
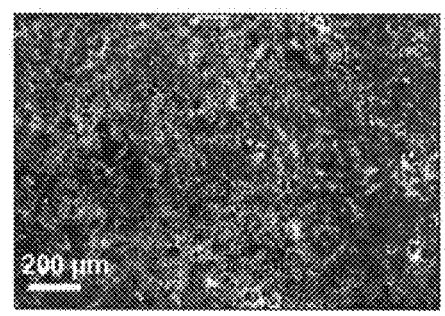

In order to confirm that the effect of the nanoparticles occurs at the stage of viral attachment, in another experiment cells were infected in the absence or presence of Au-MES NPs and the plates were kept at 4° C. for 2 hours to enable virus attachment, but not entry of the virus into the cells (Flint et al., in *Principles of Virology: Molecular Biology.* 3rd Ed. ASM Press: Washington, D.C., 2009; incorporated by reference herein in its entirety). After 2 hours, the cells were washed and overlaid with fresh media containing human γ-globulin and incubated at 37° C. for 48 hours. This procedure allowed cell-attached virions to infect and enter the cells. Results obtained after 48 hours revealed large and distinct plaques in cells that were infected in the absence of Au-MES NPs (FIG. 6C). In contrast, cells that were infected in the presence of Au-MES NPs demonstrated similar morphology to mock-infected cells and no plaques were evident (FIG. 6D), implying that the Au-MES NPs inhibited the attachment of the virus to the cell surface. However, the absence of the nanoparticles allowed attachment of the virus, therefore resulting in further inoculation and plaque formation.

Example 6

The Presence of Au-MES NPs in Cells does not Interfere with Viral Infection

Gold nanoparticles are taken up in mammalian cells in a size, shape and charge dependent manner (Chithrani et al., *Nano Lett.,* 2006, 6, 662-668; Cho et al., *Nano Lett.,* 2006, 6, 662-668; each incorporated by reference herein in its entirety). Therefore, the possibility of Au-MES NPs being taken up into the Vero cells during the experiments described in the Examples above cannot be ruled out. Inductively coupled plasma mass spectra (ICP-MS) measurements revealed that the Au-MES NPs are indeed uptaken into the cells (data not shown). In order to evaluate the effect of Au-MES NPs uptake by the cells on the anti-viral intrinsic cellular defense, cells were first treated with the nanoparticles and were then infected with the virus. Specifically, cell cultures were pre-incubated with Au-MES NPs for 24 hours, after which they were washed and overlaid with virus suspension. Untreated cell cultures were used as control. The number and size of the plaques were measured 48 hours post infection. No significant difference in the area of plaques in the presence or absence of Au-MES NPs was observed (t test, $p=0.081$; $n=300$), and the average number of plaques in each case also remained comparable (92.3±19 vs. 95.3±4 with and without Au-MES NPs, respectively), suggesting that the presence of nanoparticles in the cells does not interfere with the viral infection, and that cell susceptibility and permissivity to the viral infection are unaltered.

Example 7

Determination of the Toxicity and Broad-Spectrum Activity of the Nanoparticles in a Murine Model In order to evaluate local and systemic efficacy and toxicity of sulfonate-protected nanoparticles as used in the Examples described above in in vivo studies, the following three model systems can be used.

(i) The first model is aimed at evaluating the toxicity of the nanoparticles (NPs). A Phosphate Buffered Saline (PBS) solution composition NPs is topically applied to the eyes of mice, wherein three groups of uninfected mice (n=2 per group) are treated with different concentration of the NPs (200, 400 and 800 μg/ml NPs daily, for 7 days). The overall appearance and behavior of the mice is observed daily, as well as the conditions of their eyes and body temperatures. At day 7 of the experiment the eyes are examined microscopically and histologically.

In order to evaluate whether the NPs could specifically prevent HSV-1 infection in the eye, mice (n=8 per group) are inoculated with $2 \times 10^3$ HSV-1 plaque forming units (PFU), and are then treated as explained above with either PBS or PBS comprising three different concentrations of NPs starting at 4, 24 or 72 hours post infection. Each group of mice further receives the same treatment daily for an additional 4 days after the initial treatment. Two groups of uninfected mice, one treated with PBS alone and the other left untreated are included as well. All groups are monitored daily for signs of eye diseases. On day 7 post-infection the eyes are examined microscopically and histologically.

(ii) Anesthetized mice are cutaneously infected with HSV-1 after scarification (scratching the skin six times in a cross-hatched pattern) of shaved region. The efficacy of the topical treatments (as described for the eye model) are evaluated in terms of evolution of the lesions and number of lesions.

(iii) in order to investigate whether the NPs protect mice from genital HSV-1 and herpes simplex virus 2 (HSV-2) infection, mice are injected subcutaneously with 2 mg/ml medroxyprogesterone acetate (MPA) to increase susceptibility and reduce immune response (Kaushic et al., *J. Virology*, 2003, 77, 4558-4565; incorporated by reference herein in its entirety) 1 week prior to treatment or virus challenge. Mice are challenged intravaginally with 2×104, 104 or 5×103 PFU of virus, and nanoparticles in the form of a gel at three different concentrations are given twice on consecutive days. Following virus challenge, disease progression is monitored and graded according to five-point scale: no signs of infection, slight genital erythema and edema, moderate genital inflammation, purulent genital lesions, paralysis and death. Upon completion of the experiment, vaginal tissues is dissected and examined microscopically and histologically.

Although the teachings have been described with respect to various embodiments, it should be realized these teachings is also capable of a wide variety of further and other embodiments within the spirit and scope of the appended claims.

What is claimed is:

1. A topical pharmaceutical composition comprising water-soluble sulfonate-protected Ag- or Au-nanoparticles, or a pharmaceutically acceptable salt thereof, and a pharmaceutically acceptable carrier, wherein said composition is formulated as a gel, a cream, a paste, a lotion, a spray, a suspension, a dispersion, a salve, or an ointment.

2. The pharmaceutical composition of claim 1, wherein said nanoparticles range in size between 3-30 nm.

3. The pharmaceutical composition of claim 2, wherein said nanoparticles are in size of 3-4 nm.

4. The pharmaceutical composition of claim 1, wherein said sulfonate is a sulfonate moiety of the general formula -A-R—$SO_3H$, wherein R is a divalent hydrocarbyl; and A is —S—, —NH—, or —O—CO—, linked to said divalent hydrocarbyl at position omega ($\omega$) that is most remote from the $SO_3H$ group.

5. The pharmaceutical composition of claim 4, wherein A is —S—.

6. The pharmaceutical composition of claim 5, wherein said sulfonate moiety is a moiety of an $\omega$-mercapto $C_2$-$C_6$ alkane sulfonate.

7. The pharmaceutical composition of claim 6, wherein said sulfonate moiety is a moiety of 2-mercaptoethane sulfonate.

8. A method for treatment of an infection, condition or disorder caused by a microorganism capable of binding to heparan sulfate in an individual in need, said method comprising administering to said individual a therapeutically effective amount of a pharmaceutical composition comprising water-soluble sulfonate-protected Ag- or Au-nanoparticles or a pharmaceutically acceptable salt thereof, wherein said microorganism is a virus selected from the group consisting of a herpesvirus, a papillomavirus, a flavivirus, and human immunodeficiency virus (HIV); a bacterium selected from the group consisting of *Helicobacter pylori, Staphylococcus aureus*, and a *Streptococcus* of group A; or *Mycobacterium leprae*.

9. The method of claim 8, wherein said virus is a human papillomavirus and the infection, condition or disorder treated is genital warts, skin warts, vaginal cancer, or cervical cancer.

10. The method of claim 8, wherein said virus is HSV-1 or HSV-2, and the infection, condition or disorder treated is labial herpes, keratitis, or genital herpes.

11. The method of claim 8, wherein said bacterium is *Helicobacter pylori* and the infection, condition or disorder treated is duodenal or gastric ulcers, or stomach cancer.

12. The method of claim 8, wherein said bacterium is *Staphylococcus aureus* or a *Streptococcus* of group A, and the infection, condition or disorder treated is necrotizing fasciitis.

13. The method of claim 8, wherein said mycobacterium is *Mycobacterium leprae* and the infection, condition or disorder treated is Leprosy.

14. The method of claim 8, wherein said nanoparticles range in size between 3-30 nm.

15. The method of claim 14, wherein said nanoparticles are in size of 3-4 nm.

16. The method of claim 8, wherein said sulfonate is a sulfonate moiety of the general formula -A-R—$SO_3H$, wherein R is a divalent hydrocarbyl; and A is —S—, —NH—, or —O—CO—, linked to said divalent hydrocarbyl at position omega ($\omega$) that is most remote from the $SO_3H$ group.

17. The method of claim 16, wherein A is —S—.

18. The method of claim 17, wherein said sulfonate moiety is a moiety of an $\omega$-mercapto $C_2$-$C_6$ alkane sulfonate.

19. The method of claim 18, wherein said sulfonate moiety is a moiety of 2-mercaptoethane sulfonate.

* * * * *